(12) United States Patent
Rowe

(10) Patent No.: US 10,537,121 B2
(45) Date of Patent: Jan. 21, 2020

(54) SOLID MAPLE SYRUP COMPOSITIONS

(71) Applicant: IAF SCIENCE HOLDINGS LTD., Hamilton (BM)

(72) Inventor: John Lawrence Rowe, Charlottetown (CA)

(73) Assignee: IAF SCIENCE HOLDINGS LTD., Hamilton (BM)

( * ) Notice: Subject to any disclaimer, the term of this patent is extended or adjusted under 35 U.S.C. 154(b) by 580 days.

(21) Appl. No.: 14/414,602

(22) PCT Filed: Jul. 11, 2013

(86) PCT No.: PCT/CA2013/050537
§ 371 (c)(1),
(2) Date: Jan. 13, 2015

(87) PCT Pub. No.: WO2014/008602
PCT Pub. Date: Jan. 16, 2014

(65) Prior Publication Data
US 2015/0189899 A1 Jul. 9, 2015

Related U.S. Application Data

(60) Provisional application No. 61/671,171, filed on Jul. 13, 2012.

(51) Int. Cl.
| | | |
|---|---|---|
| *A61K 36/77* | (2006.01) | |
| *A61K 35/644* | (2015.01) | |
| *A23G 3/42* | (2006.01) | |
| *A23L 5/00* | (2016.01) | |
| *A23L 29/30* | (2016.01) | |
| *A61K 36/20* | (2006.01) | |
| *A23G 3/34* | (2006.01) | |
| *A23G 3/48* | (2006.01) | |
| *C13B 50/00* | (2011.01) | |
| *C13B 40/00* | (2011.01) | |
| *A61K 9/00* | (2006.01) | |
| *A23L 21/25* | (2016.01) | |
| *A61K 47/26* | (2006.01) | |
| *A61K 47/46* | (2006.01) | |

(52) U.S. Cl.
CPC ............ *A23G 3/42* (2013.01); *A23G 3/0014* (2013.01); *A23G 3/48* (2013.01); *A23L 5/00* (2016.08); *A23L 21/25* (2016.08); *A23L 29/30* (2016.08); *A61K 9/0056* (2013.01); *A61K 36/20* (2013.01); *A61K 47/26* (2013.01); *A61K 47/46* (2013.01); *C13B 40/007* (2013.01); *C13B 50/002* (2013.01); *A23V 2002/00* (2013.01)

(58) Field of Classification Search
CPC .............................. A61L 36/77; A61K 35/644
USPC ...................... 424/771, 172.1, 537
See application file for complete search history.

(56) References Cited

U.S. PATENT DOCUMENTS

| | | | |
|---|---|---|---|
| 2,760,870 A | * | 8/1956 | Naghski .................. A23L 21/25 |
| | | | 426/48 |
| 3,294,552 A | | 12/1966 | Topalian et al. ................ 127/30 |
| 3,627,583 A | * | 12/1971 | Troy .................... A23G 3/0289 |
| | | | 127/29 |
| 4,938,989 A | | 7/1990 | Steeves et al. |
| 6,458,763 B1 | | 10/2002 | Peterson et al. |
| 6,756,067 B2 | | 6/2004 | Swain et al. |
| 6,936,290 B2 | | 8/2005 | Swain et al. |
| 8,551,543 B2 | | 10/2013 | Beland et al. |
| 2002/0176909 A1 | | 11/2002 | Jampen |
| 2002/0197351 A1 | | 12/2002 | Swain et al. |
| 2010/0288269 A1 | | 11/2010 | Chadbourne |
| 2011/0052755 A1 | | 3/2011 | Fiorenza et al. |
| 2012/0034309 A1 | | 2/2012 | Rowe |
| 2012/0070541 A1 | | 3/2012 | Han et al. |

FOREIGN PATENT DOCUMENTS

| | | | | |
|---|---|---|---|---|
| CA | 1115270 | | 12/1981 | |
| CA | 1115270 A | * | 12/1981 | ............. C13B 10/00 |
| JP | S483387 U | | 5/1971 | |
| JP | 5558100 B2 | * | 4/1980 | ......... A61B 17/0469 |
| JP | S5558100 | | 4/1980 | |
| JP | H2222645 A | | 9/1990 | |
| JP | H9224577 A | | 9/1997 | |
| WO | 02/091854 A2 | | 11/2002 | |
| WO | WO 2010081232 | | 7/2010 | |
| WO | 2010/099617 A1 | | 9/2010 | |

OTHER PUBLICATIONS

Bulk Foods, "Honey Powder", http://www.bulkfoods.com/honey_powder.asp, retrieved Jul. 5, 2012.
PackitGourmet, "Maple Syrup Powder, Organic", http://www.packitgourmet.com/MapleSyrupPowder.html, retrieved Jan. 14, 2015.
Notification of Reasons for Refusal for JP2015-520784, dated Jun. 6, 2017.
"Series on Techniques for Effective Utilization of New Food Ingredients (33): Maltitol", *Food Science* 42 (2000) 85-98.
Office Action Issued in Corresponding Korean Application No. 10-2015-7003819, dated Jul. 22, 2019 (English Translation).
Official Communication Issued in Corresponding Indian Application No. 333/KOLNP/2015, dated Aug. 13, 2019.

* cited by examiner

*Primary Examiner* — Michael Barker
*Assistant Examiner* — Deborah A Davis
(74) *Attorney, Agent, or Firm* — Norton Rose Fulbright US LLP

(57) ABSTRACT

The present invention relates to a maple syrup product having a low water content. The maple syrup product retains the physical and palatable properties of untreated maple syrup while having a prolonged shelf-life. It can be advantageously used to sweeten beverages (such as hot beverages) and in the manufacture of pharmaceutical compositions (such as throat lozenges) and/or confectionery.

19 Claims, No Drawings

SOLID MAPLE SYRUP COMPOSITIONS

CROSS-REFERENCE TO RELATED APPLICATION

This application is a national phase application under 35 U.S.C. § 371 of International Application No. PCT/CA2013/050537 filed Jul. 11, 2013, which claims priority from U.S. provisional application Ser. No. 61/671,171 filed on Jul. 13, 2012. The entire contents of each of the above-referenced disclosures is specifically incorporated by reference herein without disclaimer.

FIELD OF THE INVENTION

This invention relates to solid maple syrup products having a low water content. The organoleptic and physical characteristics of the solid maple syrup product are very similar to those of the maple syrup. In addition, the sugars in the maple syrup product are not crystallized.

BACKGROUND

Maple syrup is obtained from boiling the xylem sap of maple trees. In cold climates, the maple trees store starch in their trunks and roots before the winter and the starch is converted to sugar that rises in the sap in the spring. Maple trees can be tapped by boring holes into their trunks and collecting the exuded sap. The sap is processed by heating to evaporate much of the water, leaving the concentrated syrup.

Maple syrup is graded according to the Canada, United States, or Vermont scales based on its density and translucency. Sucrose is the most prevalent sugar in maple syrup. In Canada, syrups must be at least 66 percent sugar and be made exclusively from maple sap to qualify as maple syrup. In the United States, a syrup must be made almost entirely from maple sap to be labeled as "maple".

Since the applications of maple syrup in a liquid form are limited, it would be highly desirable to be provided with a maple syrup product processed into a solid form and therefore having a low water content. In addition, since existing dehydrated powdered maple syrup products do not exhibit the flavor profile of the liquid maple syrup (usually because the sucrose content from an exogenous additive is too elevated), it would also be desirable to be provided with a maple syrup processed into a solid form having, as a predominant flavor, the distinct maple syrup flavor. It would also be desirable to obtain a dehydrated product which is a flowable liquid at elevated temperature (in order to facilitate handling of the product) and a solid room temperature (in order to facilitate processing and use of the product). It would also be preferable that the dehydrated maple syrup product, upon storage, does not form crystalized sugars. It would nevertheless be preferably a very versatile product that could be processed into various food, nutraceutical, dietary supplement or natural health product applications.

SUMMARY

The present invention relates to a solid maple syrup product having a low water content. The maple syrup product is a pure dried product obtained from the dehydration of a combination of maple syrup and a low-sucrose carbohydrate. The storage of the solid maple syrup does not lead to the formation of crystallized sugars. The present invention also relates to a process for obtaining the solid maple syrup product which allows to generation of a flowable dehydrated maple syrup product at elevated temperatures.

According to a first embodiment, the present invention provides a solid maple syrup product consisting essentially of a combination of maple syrup and a low-sucrose carbohydrate. As used herein, the term "consisting essentially of" indicates that the maple syrup product is composed of maple syrup and a low-sucrose carbohydrate and its usual constituents (refer to the definition of maple syrup and low-sucrose carbohydrate below) and that no further additives are required to dehydrate the product (e.g. and, in embodiments, to process it, to package it or to store it). The maple syrup product has a moisture content equal to less than about 0.5% (w/w). The maple syrup is obtained by combining a liquid maple syrup and the low-sucrose carbohydrate to obtain an initial mixture, wherein the percentage of maple syrup, on a weight basis, in the initial mixture is equal to or lower than about 66% (and in embodiments, equal to or lower than about 65% or 51%). In some embodiment, the initial mixture has a sucrose content, on a weight basis, equal to or less than 65% (w/w) (and in embodiment, equal to or less than 60%, 55%, 50%, 45%, 40%, 35% or 30%). In an embodiment, the sucrose content, on a weight basis, of the initial mixture is equal to but not higher than 65%, 60%, 55%, 50%, 45%, 40%, 35% or 30%. In an embodiment, the moisture content of the maple syrup product is equal to or less than about 0.4%, than about 0.3%, than about 0.2%, than about 0.1%, than about 0.09%, than about 0.08%, than about 0.07%, than about 0.06%, than about 0.05%, than about 0.04%, than about 0.03%, than about 0.02% or than about 0.01%. In a further embodiment, the moisture content of the maple syrup product is equal to but not higher than 0.5% (w/w), than about 0.4%, than about 0.3%, than about 0.2%, than about 0.1%, than about 0.09%, than about 0.08%, than about 0.07%, than about 0.06%, than about 0.05%, than about 0.04%, than about 0.03%, than about 0.02% or than about 0.01%. In an embodiment, the low-sucrose carbohydrate is honey and the maple syrup product obtained therefrom is a solid maple syrup/honey product. In some embodiments, the initial mixture is submitted to a dehydrating step comprising a raise in temperature (from room temperature to 85° C. for example) as well as to a partial vacuum (for example 28 inches of Hg) for a period of time sufficient to reduce the water content of the composition to at least 0.5% (for example at least 65 minutes). In the process of making the solid maple syrup product, it is preferable to generate an end-product that is a fluid (e.g. a flowable product) at 60° C. in order for allowing its deposition it into mold (for subsequent solidification at room temperature). It is also preferable to generate an end-product that is a solid at room temperature. In an embodiment, the weight ratio in the initial mixture between the initial maple syrup and honey prior to the dehydration process is at least 1:1 (respectively) and, in alternative embodiments, it can also be 3:2 and even 14:11. In additional embodiments, the sugars of the solid maple syrup product are not crystallized (e.g. they are in an uncrystallized form) even after storage (for example 3, 6, 9 or 12 months). In further embodiment, the solid maple syrup product is translucent and its color is similar to the one of the untreated maple syrup. In a further embodiment, the solid maple syrup product can be further processed once it has set into a solid (cut, crushed or powdered for example). In another embodiment, the maple syrup product can be used as a sweetener. In still another embodiment, the maple syrup product can be wrapped in a water-impermeable package. In this particular embodiment, the maple syrup product can have a storage time of three years (or more) without substantially reabsorbing water and/or forming sugar crystals.

According to a second embodiment, the present invention also provides a maple syrup composition comprising the solid maple syrup product described herein and at least one additive. Various additives can be added to the dehydrated maple syrup product (after the dehydration step). In some embodiments, the additive can be a flavor, such as, for example, a spearmint, a *eucalyptus*, a menthol and/or a lemon flavor. In other embodiment, the at least one additive can be a preservative (such as a sugar alcohol). In an embodiment, the maple syrup product can be coated with a preservative prior to packaging to favor packaging. In another embodiment, the maple syrup product or the maple syrup composition can be further processed a confectionery. In a further embodiment, the maple syrup product or the maple syrup composition can be formulated a pharmaceutical composition (such as, for example a throat lozenge).

DETAILED DESCRIPTION OF VARIOUS EMBODIMENTS

In accordance with the present invention, there is provided a solid maple syrup product having a moisture content of less than 0.5%. The maple syrup product described herein consists essentially of a liquid maple syrup and low-sucrose carbohydrate to which water has been removed. It is a pure maple syrup product to which no additive, besides the low-sucrose carbohydrate, has been added during the dehydration process. The maple syrup product is not limited to the use of any specific low-sucrose carbohydrate. However, since the maple syrup product retains the color, characteristics and the taste of untreated maple syrup, care must be taken in selecting an appropriate low-sucrose carbohydrate that will preserve the original maple syrup color, characteristics and taste. Further, the maple syrup product is not limited to any specific manufacturing technique. However, since the maple syrup product retains the color, characteristics and the taste of untreated maple syrup, care must be taken in selecting an appropriate manufacturing technique that will preserve the original maple syrup color, characteristics and taste. In addition, since dehydrated maple syrup has a tendency to set into a solid at elevated temperatures (for example at about 60° C. or more), care should be taken in selecting an appropriate manufacturing technique that will allow the dehydrated end product to be manipulated and cooled to a solid (at room temperature, for example, at a temperature between about 20° C. and about 30° C.). Further, since dehydrated maple syrup has a tendency to develop a burnt flavor when heated, care should be taken in selecting an appropriate manufacturing technique that will not allow the dehydrated end product to develop a burnt flavor or taste.

The present invention provides a solid maple syrup product consisting essentially of a combination of maple syrup and a low-sucrose carbohydrate. In a further embodiment, the maple syrup product consists of maple syrup and the low-sucrose carbohydrate. As used herein, the term "maple syrup" is referred to a syrup obtained from the boiling of the xylem sap of maple trees. The maple syrup is essentially a saturated sucrose solution lacking crystals. Three species of maple trees are predominantly used to produce maple syrup: the sugar maple (*Acer saccharum*), the black maple (*A. nigrum*), and the red maple (*A. rubrum*), because of the high sugar content (roughly two to five percent) in the sap of these species. A few other (but not all) species of maple (*Acer*) are also sometimes used as sources of sap for producing maple syrup, including the box elder or Manitoba maple (*Acer negundo*), the silver maple (*A. sacharinum*) and the big leaf maple (*A. macrophyllum*). The maple syrup that can be used in the product/compositions described herein is not limited to the sap of a single tree species. In an embodiment, the maple syrup is produced from the sap of a single maple tree species. However, in other embodiments, it may be preferable to produce the maple syrup from more than one maple tree species.

Once the sap has been collected, it is boiled down to obtain a maple syrup. To obtain pure maple syrup, the boiling step is usually conducted in the absence of chemical agents or preservatives. Maple syrup can be made by boiling sap at a temperature higher than 100° C. (e.g. 104.1° C. for example) to a sugar concentration of about 66%. Boiling the syrup is a tightly controlled process, which ensures appropriate sugar content. Syrup boiled too long will eventually crystallize (and form maple sugar), whereas under-boiled syrup will be watery and will quickly spoil. The finished syrup usually has a density of 66° on the Brix scale. The maple syrup can be filtered to remove particles such as sugar sand, crystals made up largely of sugar and calcium malate. Optionally, filtered maple syrup can be graded and packaged (preferably while still hot, usually at a temperature of 82° C. or greater). The chemical composition of maple syrup varies depending on sap source, season and production methods. Storage conditions may also influence final composition, with the proportion of disaccharides increasing over time.

The sole ingredient in maple syrup is the sap from the xylem of maple or trees. It consists primarily of sucrose and water, with small amounts of other sugars. Organic acids, the most notable one being malic acid, make the syrup slightly acidic. Maple syrup has a relatively low mineral content, consisting largely of potassium and calcium, but also contains nutritionally significant amounts of zinc and manganese. Maple syrup also contains trace amounts of amino acids, which may contribute to the "buddy" flavor of syrup produced late in the season, as the amino acid content of sap increases at this time. Additionally, maple syrup contains a wide variety of volatile organic compounds, including vanillin, hydroxybutanone, and propionaldehyde. The water content of maple syrup is usually between 25 to 35% (w/w).

The maple syrup that can be used in the products and compositions described herein does not include unboiled sap or unboiled processed sap, such as, for example, vacuum-dried sap or spray-dried sap. In addition, it is preferable that the maple syrup that is included in the original mixture be substantially free of carbohydrate crystals.

As indicated herein, the maple syrup product also contains a low-sucrose carbohydrate. As used herein, a "low-sucrose" carbohydrate is a carbohydrate having the majority of its sugars that are not sucrose. Further, the low-sucrose carbohydrate, once dehydrated, should not provide more than 5%, more than 2% or more than 1% sucrose (on a weight basis) of the final product. The low-sucrose carbohydrate is preferably provided in the initial mixture as a liquid or a solution. In an embodiment, the low-sucrose carbohydrate can be honey. In another embodiment, the low-sucrose carbohydrate does not comprise any sucrose. Since the combination of glucose and maple syrup lead to the formation of sugar crystals upon storage, in another embodiment, the low-sucrose carbohydrate is not a pure glucose liquid solution.

It is believed that the addition of a low-sucrose carbohydrate to the maple syrup prior to dehydration will allow to decrease the final sucrose content of the maple syrup product (when compared to pure maple syrup). It is believed that by limiting the content in maple syrup in the product (to a percentage equal to or less than 66% in the initial mixture) it will allow the formation of a dehydrated maple syrup product that is workable (e.g. flowable at temperatures equal to or higher than 60° C.) and that, upon storage, will not have a tendency to form sugar crystals. Prior to the dehydration process, the low-sucrose carbohydrate can be provided in a solid or a liquid form. The low-sucrose carbohydrate used to manufacture the maple syrup product can be derived from a single source or from a combination of sources depending on the desired properties of the final product.

In order to obtain the maple syrup product and compositions described herein, it is necessary to first combine the maple syrup and the low-sucrose carbohydrate (generally in the form of a solution). The proportions of maple syrup and the low-sucrose carbohydrate solution in the original untreated mixture can vary, but the initial mixture of maple syrup and low-sucrose carbohydrate contains a percentage of maple syrup (on a weight basis) equal to or less than 66%. In an embodiment, this initial mixture has a sucrose content equal to or less than about 65% (and preferably less than about 50%). In an embodiment, the same amount of maple syrup and the low-sucrose carbohydrate solution are admixed. In another embodiment, more amount of the maple syrup is provided to the initial mixture when compared to the low-sucrose carbohydrate. In embodiments, the weight ratio of maple syrup to the low-sucrose carbohydrate is at least equal (1:1) or higher (for example, 3:2, 4:3, 5:4, 6:5, 7:6, 8:7, 9:8, 10:9, 11:10, 12:11, 13:12 or 14:11). In other embodiment, the percentage of maple syrup, on a weight basis, in the initial mixture is equal to or lower than about 66%, 65%, 60%, 55%, 54%, 53%, 52% or 51%; whereas the percentage of the low-sucrose carbohydrate, on a weight basis in the initial mixture, is equal to or higher than about 34%, 35%, 40%, 45%, 46%, 47%, 48% or 49%. In a preferable embodiment, the original mixture (or the individual components of the original mixture) is not submitted to any preparatory steps (such as, for example, enzymatic treatment), prior to its dehydration. Once the initial mixture has been provided, it is processed in order to reduce its moisture content (e.g. dehydration step, such as, for example, spray-drying, vacuum drying, etc.) to at least about 0.5% to obtain a maple syrup product in solid form.

In one advantageous embodiment, it is possible to use a combination of vacuum and heat treatment steps to remove most of the water content of the initial mixture of maple syrup and the low-sucrose carbohydrate solution. As used herein "solid maple syrup product" refers to a substance derived from a combination of maple syrup and the low-carbohydrate solution that is not liquid nor gaseous and that can be used as a source of nourishment. After the dehydration process has been completed, the dehydrated maple syrup product is a flowable liquid at elevated temperatures (for example, at temperature higher than about 60° C.) allowing it in being easily handled (e.g. deposited in a mold). After the dehydration process has been completed, the maple syrup product is a cooled into a translucent solid at room temperature (e.g. at a temperature between about 20° C. to about 30° C.) allowing it in being easily used or further processed.

In an embodiment, the low-sucrose carbohydrate is honey. In those embodiments, a dehydrated maple syrup/honey product (solid at room temperature) is produced. The maple syrup/honey products and compositions described herein essentially consists in a combination of maple syrup and honey. As used herein, the term "honey" is referred to as a product prepared by bees from plant nectars, from plant secretions and from excretions of plant sucking insects ("honeydew"). Honey can also be referred to as the nectar and saccharine exudations of plants gathered, modified and stored by the honey bee. The chemical composition of honey varies depending on nectar source, season and production methods. Storage conditions may also influence final composition, with the proportion of disaccharides increasing over time. Fructose and glucose are present in relatively equal amounts and are the two major sugars present in honey (approximately 70% w/w). Honey also contains lesser amounts of sucrose (approximately 1%), other disaccharides and oligosaccharides. Gluconic acid, other acids and small amounts of proteins, enzymes (including glucose oxidase), amino acids and minerals may also be present. Potassium is the major mineral present. Honey is usually mildly acidic with a pH around 3.9. Moisture content is low (between 13% to 26% w/w), as is water activity (0.562-0.62).

In the manufacturing process described herein dehydrated solid honey or liquid honey can be used. In the latter embodiment, it is contemplated that any liquid honey can be used in the manufacture of the maple syrup/honey product. The liquid honey can be raw (e.g. untreated), semi-processed (such as strained or filtered honey) or processed (e.g. pasteurized). The honey product can be made with liquid honey originating from any nectar source. Nectar sources include, but are not limited to, *acacia*, alfalfa, apple, blueberry, buckwheat, canola, clover, cotton, cranberry, dandelion, gall berry, goldenrod, grape, mesquite, clover, milkweed, *palmetto*, prune, rape, raspberry, sage, sourwood, sunflower, and/or tupelo. The liquid honey used to manufacture the maple syrup/honey product can be derived from a single nectar source or from a combination of nectar sources depending on the desired properties of the final product.

In order to obtain the maple syrup/honey product and compositions described herein, it is necessary to first combine the maple syrup and the honey. The proportions of maple syrup and honey in the original untreated mixture can vary, but the initial mixture of maple syrup and liquid honey contains, on a weight basis, either the same amount of maple syrup and honey or more maple syrup than honey. In embodiments, the weight ratio of maple syrup to honey is at least equal (1:1) or higher (for example, 3:2, 4:3, 5:4, 6:5, 7:6, 8:7, 9:8, 10:9, 11:10, 12:11, 13:12 or 14:11). In other embodiment, the percentage of maple syrup, on a weight basis, in the initial mixture is equal to or higher than about 50%, 51%, 52%, 53%, 54%, 55%, 60% or 65%; whereas the percentage of honey, on a weight basis in the initial mixture, is equal to or less than about 50%, 49%, 48%, 47%, 46%, 45%, 40% or 35%. In a preferable embodiment, the original mixture (or the individual components of the original mixture) is not submitted to any preparatory steps (such as, for example, enzymatic treatment), prior to its dehydration. Once the mixture of maple syrup/honey has been provided, it is processed in order to reduce its moisture content (e.g. dehydration step, such as, for example, spray-drying, vacuum drying, etc.) to at least about 0.5% to obtain a maple syrup/honey product in solid form.

In one advantageous embodiment, it is possible to use a combination of vacuum and heat treatment steps to remove most of the water content of the original mixture of maple syrup and honey. As used herein "solid maple syrup/honey product" refers to a substance derived from a combination of maple syrup and honey that is not liquid nor gaseous and that can be used as a source of nourishment. After the dehydration process has been completed, the dehydrated maple syrup/honey product is a flowable liquid at elevated temperatures (for example, at temperature higher than about 60°

C.) allowing it in being easily handled (e.g. deposited in a mold). After the dehydration process has been completed, the maple syrup/honey product is a cooled into a translucent solid at room temperature (e.g. at a temperature between about 20° C. to about 30° C.) allowing it in being easily used or further processed.

In yet another embodiment, the maple syrup/honey product described herein is a pure and/or dried maple syrup/honey product. As used herein, the term "pure" maple syrup/honey product refers to a product that is free or substantially free from exogenous additives (such as, for example, exogenous polysaccharide (trehalose, sucrose, glucose isomalt) with respect to the original liquid maple syrup/honey combination.

As it will be shown below in the Example section, a dehydrated maple syrup-containing product can be difficult to manipulate (even at temperatures equal to or higher than 60° C.) because it sets into a solid form at elevated temperature, it forms crystals during storage and/or is not fluid enough to be deposited or poured. As also shown below in the Example section, a dehydrated maple syrup-containing product can also develop a burnt flavor during the dehydration process.

In an embodiment, the maple syrup product described herein is a dried maple syrup product. A "dried" or "dehydrated" maple syrup product refers to the fact that the moisture content is limited to no more than about 0.5% w/w, about 0.4% w/w, about 0.3% w/w, about 0.2% w/w, about 0.1% w/w, about 0.09% w/w, about 0.08% w/w, about 0.07% w/w, about 0.06% w/w, about 0.05% w/w, about 0.04% w/w, about 0.03% w/w, about 0.02% w/w or about 0.01% w/w.

The person skilled in the art can easily assess the percentage of moisture in a maple syrup product using methods readily known in the art. The moisture content of a food product is usually defined through the following formula:

$$\% \text{ moisture} = (m_w/m_{sample}) \times 100$$

In this formula, $m_w$ is the mass of the water and $m_{sample}$ is the mass of the sample. The mass of water is related to the number of water molecules ($n_W$) by the following formula:

$$M_w = n_w M_w / N_A,$$

In this formula, $M_w$ is the molecular weight of water (18.0 g per mole) and $N_A$ is Avodagro's number ($6.02 \times 10^{23}$ molecules per mole). In principle, the moisture content of a maple syrup product can therefore be determined accurately by measuring the number or mass of water molecules present in a known mass of sample. When determining the moisture content of a food it is important to prevent any loss or gain of water. For this reason, exposure of a sample to the normal atmosphere, ambient temperature and excessive temperature fluctuations, should be minimized.

In one embodiment, a spectroscopic method can be used to determine the moisture content of the maple syrup product. Spectroscopic methods utilize the interaction of electromagnetic radiation with materials to obtain information about their composition, e.g., X-rays, UV-visible, NMR, microwaves and infra-red (IR). The spectroscopic methods developed to measure the moisture content of foods are based on the fact that water absorbs electromagnetic radiation at characteristic wavelengths that are different from the other components in the food matrix. Microwave and infra-red radiation are absorbed by materials due to their ability to promote the vibration and/or rotation of molecules. The analysis is carried out at a wavelength where the water molecules absorb radiation, but none of the other components in the food matrix do. A measurement of the absorption of radiation at this wavelength can then be used to determine the moisture content: the higher the moisture content, the greater the absorption. Instruments based on this principle are commercially available and can be used to determine the moisture content in a few minutes or less.

In another embodiment, a chemical reaction, such as a colometric reaction, can be used for the determination of moisture in the maple syrup product. The Karl Fischer titration is often used for determining the moisture content of foods that have low water contents (e.g. dried fruits and vegetables, confectionery, coffee, oils and fats). It is based on the following reaction:

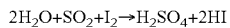

$$2H_2O + SO_2 + I_2 \rightarrow H_2SO_4 + 2HI$$

This reaction was originally used because HI is colorless, whereas $I_2$ is a dark reddish brown color, hence there is a measurable change in color when water reacts with the added chemical reagents. Sulfur dioxide and iodine are gaseous and would normally be lost from solution. For this reason, the above reaction has been modified by adding solvents (e.g., $C_5H_5N$) that keep the $S_2O$ and $I_2$ in solution, although the basic principles of the method are the same. The food to be analyzed is usually placed in a beaker containing solvent and is then titrated with Karl Fischer reagent (a solution that contains iodine). While any water remains in the sample the iodine reacts with it and the solution remains colorless (HI), but once all the water has been used up any additional iodine is observed as a dark red brown color ($I_2$). The volume of iodine solution required to titrate the water is measured and can be related to the moisture content using a pre-prepared calibration curve. The precision of the technique can be improved by using electrical methods to follow the end-point of the reaction, rather than observing a color change.

One particular advantage of the solid maple syrup product described herein is that, during its dehydration process, no additives are being added to facilitate water removal, to facilitate flowing of the dehydrated product into molds, to limit the formation of sugar crystals during storage and/or to limit the adhesion of the product to its packaging membrane.

When the maple syrup product is wrapped in a water-impermeable package, its storage time is of about three years or even more (depending on the WVTR of the package). During storage, the product does not substantially reabsorb water and as such its water content is substantially constant. As used herein, a maple syrup product that does not "substantially" reabsorb water is a maple syrup product that possesses a water content of less than about 0.5% w/w during its storage. As indicated above, when the water content of the maple syrup product exceeds 0.5% w/w, the maple syrup product becomes tacky.

Another advantage of the solid maple syrup product described herein is that the majority of the sugars present are in an uncrystallized form. As used herein the term "uncrystallized" refer to the absence of sugar crystals that can be felt in the mouth and/or visible to the naked eye. The maple syrup product has a smooth texture and does not contain granulated maple syrup crystals which can be seen by the naked eye or be felt in the mouth. In an embodiment, the maple syrup described herein does not contain sugar crystals even after long-term storage (e.g. 3, 6, 9, 12 or 36 months).

A further advantage of the maple syrup product described herein is that, once cooled at room temperature after vacuum dehydration (but prior to other processing steps), it is a translucent product having the color characteristics of the original maple syrup (e.g. shades of yellow and brown).

However, upon water removal, it is assumed that the solid maple syrup product will have an increase in color (with respect to the original maple syrup) and that the shade of product could be perceived as different (e.g. darker) than in the untreated liquid maple syrup.

Another advantage of the maple syrup product described herein is that, once cooled at room temperature after vacuum dehydration (but prior to other processing steps) it has, as a predominant flavor, the organoleptic properties of the original maple syrup (flavor, intensity, mouth feel). In some embodiments, it is also possible to distinguish, as a minor flavor, the organoleptic properties of the low-sucrose carbohydrate (e.g. honey in some embodiments). However, upon water removal, it is assumed that the solid maple syrup product will have an increase in flavor intensity and stickiness (with respect to the original maple syrup) and that the sweetness level of product could be perceived as different (e.g. heightened) than in the untreated liquid maple syrup.

As indicated above, the solid maple syrup product is not limited to a specific manufacturing technique. In one advantageous embodiment and as shown below, the liquid maple syrup is submitted to vacuum drying to lower its water content and generate the maple syrup product. Besides the addition of the low-sucrose carbohydrate source, the liquid maple syrup is not supplemented with an exogenous source of additive or enzymatically treated prior to its dehydration. The time, temperature and pressure variables used should be designed to generate a solid maple syrup product having similar organoleptic characteristics as the original liquid (e.g. hydrated) maple syrup. The time, temperature and pressure variables used should also be designed to generate a dehydrated maple syrup that is in liquid form at elevated temperature (e.g. at temperatures above 60° C. and below 90° C.) in order to facilitate/enable its subsequent processing and in a solid form at room temperature (e.g. at temperatures between 20° C. to 30° C.).

In an embodiment, the maple syrup/low-sucrose carbohydrate can be heated from ambient temperature of less than 90° C. (e.g. 85° C. for example). While the temperature is gradually increased, a pressure of 28 inHg is simultaneously applied to the combination of maple syrup/low-sucrose carbohydrate. This vacuum is maintained until the moisture content reaches a specific threshold (for example equal to or less than 0.5%, 0.4%, 0.3%, 0.2%, 0.1%, 0.09%, 0.08%, 0.07%, 0.06%, 0.05%, 0.04%, 0.03%, 0.02% or 0.01%), depending on the final application of the product. Depending on the moisture content of the original maple syrup/low-sucrose carbohydrate combination, the dehydration process for the production of the solid maple syrup/low-sucrose carbohydrate product can last at least 60 minutes, at least 70 minutes, at least 80 minutes, at least 90 minutes or at least 95 minutes. The dehydration process is preferably conducted under constant stirring (or any other techniques known in the art) to evenly distribute the temperature in the maple syrup/low-sucrose carbohydrate that is being dehydrated and/or to avoid burning of the dehydrated maple syrup. As it is known in the art, the temperature, vacuum and time parameters can be modified to reach the desired temperature. These parameters will also depend on the amount of maple syrup/low-sucrose carbohydrate that is being processed as well as the content of original the liquid maple syrup (such as its moisture content).

Once the solid maple syrup product has been dehydrated (e.g. reached its moisture content of less than 0.5% as indicated above), it can be deposited into molds and cooled at room temperature. In some embodiments, the dehydrated maple syrup product is deposited into molds. The deposition into mold is preferably performed when the dehydrated maple syrup product is at a temperature higher than the temperature it sets into a solid, for example, at temperatures equal to or higher than 60° C. (and preferably lower than 90° C.). The cooled solid maple syrup product can be manufactured to any size that is convenient for the end-use, for example in formats ranging from μg to kg.

Optionally, the solid maple syrup product can be packaged. Because of the hygroscopic nature of the dehydrated maple syrup product, it will tend to reabsorb water if it is not placed in a water impermeable package. For example, depending on the relative humidity of the environment, if the product is left at ambient temperature, within a couple of days, it will tend to become tacky and, within a couple of weeks, it will tend to become sticky. As such, in order to prolong the shelf life of the product, it can be packaged in a water-impermeable membrane. As used herein, a "water-impermeable package" or "water-impermeable membrane" refers to a material that limits the transmission of water vapor. In an embodiment, the water vapor transmission rate (VWTR) of the "water-impermeable" package or membrane is below 0.1 gm/100 in$^2$ or below about 0.01 gm/100 in$^2$. Because the maple syrup product can be used as a food or as a food additive, the package can be of food or pharmaceutical grade. Further, since the package can optionally be submitted to heat to seal it around the maple syrup product, the package or membrane can also be resistant to heat.

Once the solid maple syrup product has set into a solid form (by cooling down at room temperature for example), it can optionally be further processed into a maple syrup composition. For example, in an embodiment, it is contemplated that a flavor can be added to the maple syrup product described after it has been dehydrated (in embodiments, prior to the product setting into a solid). The added flavor may be, for example, a sweet or a savory flavor. Sweet flavors include, but are not limited to fruits (peach, pear, apple), citrus (orange, lemon, lime), berry (raspberry, strawberry, blueberry), spice (vanilla, cinnamon, clove, lavender), caramel, butterscotch, maple, mint (spearmint, menthol). Savory flavors include, but are not limited to, ginger, pepper (black, white, pink, green, hot), etc. Other flavors, such as coffee, tea, herbal tea and/or alcohol, can also be added. In an embodiment, the flavor can be derived from an oil, a powder and/or an extract (such as, for example, an alcohol extract). In one preferred embodiment, the solid maple syrup product is combined with a menthol and a *eucalyptus* flavor.

In other optional or complementary embodiments, a preservative can be added to the dehydrated maple syrup product (after its dehydration) to prolong its self-life, delay or limit water reabsorption and/or preserve the formation of crystals. Such preservative can be an emulsifier, an anti-sticking agent and/or a stabilizer, including, but not limited to bee wax, carnauba wax, a sugar (such as trehalose and/or sucrose), a sugar alcohol or polyol (such as, for example, methanol, ethylene glycol, glycerol, erythritol, threitol, arabitol, ribitol, xylitol, mannitol, sorbitol, galactitol, iditol, volemitol, fucitol, inositol, maltitol, lactitol, isomalt, maltotriitol, maltotetraitol and/or polyglycitol) or other food/pharmaceutical processing aids. In one exemplary embodiment, the solid maple syrup product (optionally previously crushed or powdered) is admixed with a processing aid (for example a sugar alcohol) for delivering a therapeutic product, a nutraceutical or a natural health product.

In other optional or complementary embodiments, a preservative can be added to the dehydrated maple syrup product to prolong its self-life, delay or limit water reabsorption and/or preserve the formation of crystals. Such preservative can be an emulsifier, an anti-sticking agent and/or a stabilizer, including, but not limited to bee wax, carnauba wax or other food/pharmaceutical processing aids. Such preservative can be admixed with the dehydrated and flowable maple syrup product. Alternatively, the preservative can be coated on the dehydrated and solid (e.g. cooled) maple syrup product to facilitate the packaging process. Exemplary preservatives that can be used to coat the maple syrup product include, but are not limited to maltodextrin and/or a flavoring (e.g. preferably in a powder form).

The solid maple syrup product can be used without any further processing, usually as a sweetener in food applications. However, the solid maple syrup product can be further processed for use in other food applications (such as confectionary, dessert topping and/or sweet ingredient) as well as in pharmaceutical applications (such as throat lozenges). In such instances, the solid maple syrup product can be further powdered, crushed, ground and/or granulated for these additional applications.

Particles can thus be made from the solid maple syrup product and used in various applications. For example, when a coarser particle is required, the solid maple syrup can be processed into a "granular" form particles having a size distribution that ranges between about 0.25 and 2 mm. On the other hand, when a finer particle is needed, the solid maple syrup product can be processed into a "powder" form particles having a size distribution that ranges between 62.5 to 125 μm. The size distribution of the particles can be assessed by the techniques known in the art, such as the Gates-Gaudin-Schuhmann method, the Rosin-Rammler method, the modified Gaudin-Meloy method, the Log-normal method and/or the modified beta method. Similar to what has been indicated above for the solid maple syrup products, the particles of the solid maple syrup product can also be packaged in a water-impermeable membrane to slow down, delay or prevent water reabsorption.

The maple syrup product or the maple syrup composition as described herein can be advantageously used to sweeten a beverage. When the solid maple syrup product is placed in an aqueous-based beverage, it reabsorbs water and dissolves to sweeten the beverage. The application of the maple syrup product is not limited to a specific type of beverage or to beverages having a specific temperature.

Because of the excellent palatable properties of the solid maple syrup, the maple syrup product or the maple syrup composition described herein can be further processed into a confectionery. In order to introduce the solid maple syrup product into a confectionery, and as indicated above, it can be physically processed (crushed, powdered, coated in a solution) and/or flavors can be added. Alternatively or concomitantly, the manufacturing process of the product can also be altered to introduce additional components of the confectionery.

Further, the solid maple syrup product can be formulated into a pharmaceutical composition to improve its taste (e.g. providing a sweet taste).

The present invention will be more readily understood by referring to the following examples which are given to illustrate the invention rather than to limit its scope.

Example I—Production of Solid Maple Syrup Products

The ingredients used in the following protocols are 100% pure maple syrup (having an initial water content between 26 and 32%), 100% pure honey (having an initial water content between 14 and 18%), 100% liquid glucose, pure trehalose, pure isomalt and/or pure sucrose. When two ingredients were combined, they were first stirred to ensure a homogenous mixture, poured into a reactor vessel and a vacuum was applied. When only maple syrup was used, it was directly poured into a reactor vessel and a vacuum was applied. The time and temperatures that were applied are presented in the protocols. The content of the reaction vessel is stirred with a rotating paddle throughout process at a constant rate of 30 rpm. Prior to dispensing the evaporated/dehydrated end product maple in the molding trays, an aliquot was removed to determine the moisture content using and infra-red moisture meter in order to rapidly assess the moisture content. The evaporated/dehydrated end product was then tentatively deposited into molding trays and cooled to room temperature.

Protocol A.

Pure maple syrup was submitted to a vacuum dehydration at a temperature of 98° C., under a vacuum of 28 inches of Hg (at T=0). After 60 minutes, the vacuum was released and the product was poured into molds. At the end of the process, the product was solid at a temperature of 90° C. and could not be removed from the reaction vessel. The end-product did not have any distinguishable fluidity. When heat was applied to remove the end product from the vessel, it caused a burnt flavor in the product. The moisture content of the end product could not be determined.

TABLE A

Time and temperature parameters of protocol A.

| Time (minutes) | Temperature (° C.) |
|---|---|
| 0 | 60 |
| 5 | 60 |
| 10 | 70 |
| 15 | 80 |
| 20 | 90 |
| 25 | 95 |
| 30 | 95 |
| 35 | 98 |
| 40 | 98 |
| 45 | 98 |
| 50 | 98 |
| 55 | 98 |
| 60 | 98 |

Protocol B.

Pure maple syrup was combined with liquid glucose in an attempt to improve fluidity of end product and/or delay the setting of a solid form. Five different w/w ratios of glucose to maple syrup were tested (1:9, 1:4, 3:7, 2:3 and 1:1). The maple syrup/glucose mixture was submitted to a vacuum dehydration at a temperature of 90° C., under a vacuum of 28 inches of Hg (at T=0), as provided in Table B. After 50 minutes, the vacuum was released and the product was tentatively poured into molds. The use of glucose at ratios 1:9, 1:4 and 3:7 did not improve fluidity (e.g. fluidity was considered poor) and did not provide an end-product that can be poured/deposited in the molds. The use of glucose ratios of 2:3 and 1:1 slightly improved fluidity, however it did not provide an end-product that can be poured/deposited in the molds. The moisture content of the end product could not be determined.

TABLE B

Time and temperature parameters of protocol B.

| Time (minutes) | Temperature (° C.) |
|---|---|
| 0 | 45 |
| 5 | 50 |
| 10 | 55 |
| 15 | 60 |
| 20 | 65 |
| 25 | 70 |
| 30 | 75 |
| 35 | 80 |
| 40 | 85 |
| 45 | 90 |
| 50 | 90 |

Protocol C.

Pure maple syrup was dehydrated at a lower temperature and for a longer period of time in an attempt to improve fluidity/flavor of the end product and/or delay the setting of a solid form. The maple syrup was submitted to a vacuum dehydration at a temperature of 75° C., under a vacuum of 28 inches of Hg (at T=0), as provided in Table C. Vacuum was released after 50, 60 or 70 minutes and the product was tentatively poured into molds. In each trial (50, 60 or 70 minutes), upon vacuum release, the end-product solidified in the reaction vessel and could not be poured/deposited in the molds. The moisture content of the end product could not be determined.

TABLE C

Time and temperature parameters of protocol C.

| Time (minutes) | Temperature (° C.) |
|---|---|
| 0 | 45 |
| 5 | 50 |
| 10 | 55 |
| 15 | 60 |
| 20 | 65 |
| 25 | 70 |
| 30 | 75 |
| 35 | 75 |
| 40 | 75 |
| 45 | 75 |
| 50 | 75 |
| 55 | 75 |
| 60 | 75 |
| 65 | 75 |
| 70 | 75 |

Protocol D.

Pure maple syrup was combined with trehalose in an attempt to improve fluidity of end product and/or delay the setting of a solid form. Five different w/w ratios of trehalose to maple syrup were tested (1:9, 1:4, 3:7, 2:3 and 1:1). The maple syrup/trehalose mixture was submitted to a vacuum dehydration at a temperature of 80° C., under a vacuum of 28 inches of Hg (at T=0), as provided in Table D. After 65 minutes, the vacuum was released and the product was tentatively poured into molds. The use of trehalose at any ratio did not improve fluidity (e.g. fluidity was considered poor) and did not provide an end-product that can be poured/deposited in the molds. The moisture content of the end product could not be determined.

TABLE D

Time and temperature parameters of protocol D.

| Time (minutes) | Temperature (° C.) |
|---|---|
| 0 | 30 |
| 5 | 35 |
| 10 | 40 |
| 15 | 45 |
| 20 | 50 |
| 25 | 55 |
| 30 | 60 |
| 35 | 65 |
| 40 | 70 |
| 45 | 75 |
| 50 | 80 |
| 55 | 80 |
| 60 | 80 |
| 65 | 80 |

Protocol E.

Pure maple syrup was combined with isomalt in an attempt to improve fluidity of end product and/or delay the setting of a solid form. Five different w/w ratios of isomalt to maple syrup were tested (1:9, 1:4, 3:7, 2:3 and 1:1). For ratios 1:4, 3:7, 2:3 and 1:1, isomalt had to be dissolved in water before adding and mixing with maple syrup (for every 10 g of isomalt 15 g of $H_2O$ was added). The maple syrup/isomalt mixture was submitted to a vacuum dehydration at a temperature of 80° C., under a vacuum of 28 inches of Hg (at T=0), as provided in Table E. After 65 minutes, the vacuum was released and the product was tentatively poured into molds. The use of isomalt at any ratio did not improve fluidity (e.g. fluidity was considered poor) as the end-product solidified upon vacuum release. The moisture content of the end product could not be determined.

TABLE E

Time and temperature parameters of protocol E.

| Time (minutes) | Temperature (° C.) |
|---|---|
| 0 | 30 |
| 5 | 35 |
| 10 | 40 |
| 15 | 45 |
| 20 | 50 |
| 25 | 55 |
| 30 | 60 |
| 35 | 65 |
| 40 | 70 |
| 45 | 75 |
| 50 | 80 |
| 55 | 80 |
| 60 | 80 |
| 65 | 80 |

Protocol F.

Pure maple syrup was combined with sucrose in an attempt to improve fluidity of end product and/or delay the setting of a solid form. A single ratio of sucrose to maple syrup was tested (1:9). The maple syrup/sucrose mixture was submitted to a vacuum dehydration at a temperature of 80° C., under a vacuum of 28 inches of Hg (at T=0), as provided in Table F. Forty-five minutes after applying the vacuum, crystals were visualized in the partly-dehydrated product. Sixty minutes after applying the vacuum, the product was tentatively poured into molds. The use of sucrose did not improve fluidity (e.g. fluidity was considered poor) as the end-product crystallized and solidified upon vacuum release. The moisture content of the end product could not be determined.

TABLE F

Time and temperature parameters of protocol F.

| Time (minutes) | Temperature (° C.) |
|---|---|
| 0 | 30 |
| 5 | 35 |
| 10 | 40 |
| 15 | 45 |
| 20 | 50 |
| 25 | 55 |
| 30 | 60 |
| 35 | 65 |
| 40 | 70 |
| 45 | 75 |
| 50 | 80 |
| 55 | 80 |
| 60 | 80 |
| 65 | 80 |

Protocol G.

Pure maple syrup was combined with honey in an attempt to improve fluidity of end product and/or delay the setting of a solid form. Five different w/w ratios of honey to maple syrup were tested (1:9, 1:4, 3:7, 2:3 and 1:1). The maple syrup/honey mixture was first heated to 60° C. and submitted to a vacuum dehydration at a temperature of 90° C., under a vacuum of 28 inches of Hg (at T=0), as provided in Table G. After 65 minutes, the vacuum was released and the product was tentatively poured into molds. The use of honey to maple syrup ratio of 1:9, 1:4 and 3:7 did not improve fluidity (e.g. fluidity was considered poor) as the end-product solidified upon vacuum release. The use of honey to maple syrup ratio of 2:3 and 1:1 did improve fluidity as the end-product could be successfully poured into molds and subsequently cooled to a solid state. The moisture content of the end product was determined, using and infra-red moisture meter to less than 0.05%.

TABLE G

Time and temperature parameters of protocol G.

| Time (minutes) | Temperature (° C.) |
|---|---|
| 0 | 60 |
| 5 | 65 |
| 10 | 70 |
| 15 | 75 |
| 20 | 80 |
| 25 | 85 |
| 30 | 85 |
| 35 | 85 |
| 40 | 85 |
| 45 | 85 |
| 50 | 85 |
| 55 | 85 |
| 60 | 90 |
| 65 | 90 |

Protocol H.

Pure maple syrup was combined with honey at a ratio of 14:11 (w/w) respectively. The maple syrup/honey mixture was submitted to a vacuum dehydration at a temperature of 85° C., under a vacuum of 28 inches of Hg (at T=0), as provided in Table H. After 95 minutes, the vacuum was released and the product was poured into molds. The end product was fluid at the end of the dehydration process and settle into a solid at room temperature. Once cooled, the end product is translucent (e.g. glass-like), solid (e.g. manipulatable) and stable enough to be deposited into molds, cooled down and packaged. The moisture content of the end product was determined, using and infra-red moisture meter, to less than 0.05%.

TABLE H

Time and temperature parameters of protocol H.

| Time (minutes) | Temperature (° C.) |
|---|---|
| 0 | 35 |
| 5 | 45 |
| 10 | 55 |
| 15 | 60 |
| 20 | 65 |
| 25 | 70 |
| 30 | 75 |
| 35 | 75 |
| 40 | 75 |
| 45 | 75 |
| 50 | 80 |
| 55 | 80 |
| 60 | 80 |
| 65 | 80 |
| 70 | 85 |
| 75 | 85 |
| 80 | 85 |
| 85 | 85 |
| 90 | 85 |
| 95 | 85 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A solid maple syrup product consisting essentially of a combination of maple syrup and honey, wherein sugars of the solid maple product are in an uncrystallized form and the solid maple product has a moisture content equal to or less than about 0.5% (w/w), wherein the maple syrup product is obtained by a process comprising:
    combining a liquid maple syrup and honey to obtain an initial mixture, wherein the weight ratio of maple syrup to honey, on a weight basis, in the initial mixture is at or between 1:1 and 3:2; and
    dehydrating the initial mixture.

2. The solid maple syrup product of claim 1, wherein the moisture content is equal to or less than about 0.3%.

3. The solid maple syrup product of claim 1, wherein the moisture content is equal to or less than about 0.1%.

4. The solid maple syrup product of claim 1, wherein the moisture content is equal to or less than about 0.05%.

5. The solid maple syrup product of claim 1, wherein the moisture content is equal to or less than about 0.01%.

6. The solid maple syrup product of claim 1, wherein the weight ratio of maple syrup to honey in the initial mixture is about 1:1.

7. The solid maple syrup product of claim 1, wherein the weight ratio of maple syrup to honey in the initial mixture is about 3:2.

8. The solid maple syrup product of claim 1, wherein the dehydrating step further comprises submitting the initial mixture to a vacuum of at least 28 inHg, to a raise in temperature of at least 85° C. and for a period of time of at least 65 minutes so as to obtain a dehydrated maple syrup product.

9. The solid maple syrup of claim 8, wherein the process further comprises depositing the dehydrated maple syrup product in a mold.

10. The solid maple syrup of claim 9, wherein the process further comprises cooling the deposited dehydrated maple syrup to the solid maple syrup product at room temperature.

11. The solid maple syrup product of claim 10, wherein the process further comprises processing the solid maple syrup product in a powder.

12. A maple syrup composition comprising the solid maple syrup product of claim 1 and at least one an additive.

13. The maple syrup composition of claim 12, wherein the at least one additive comprises a flavor.

14. The maple syrup composition of claim 13, wherein the flavor is selected from the group consisting of spearmint, *eucalyptus*, menthol and lemon or a combination of *eucalyptus* and menthol.

15. The maple syrup composition of claim 12, wherein the at least one additive comprises a preservative.

16. The maple syrup composition of claim 15, wherein the preservative is a sugar alcohol.

17. The maple syrup composition of claim 12, wherein the composition is a confectionery.

18. The maple syrup composition of claim 12, wherein the composition is a pharmaceutical composition.

19. The maple syrup composition of claim 18, wherein the composition is a throat lozenge.

\* \* \* \* \*

UNITED STATES PATENT AND TRADEMARK OFFICE
CERTIFICATE OF CORRECTION

PATENT NO. : 10,537,121 B2
APPLICATION NO. : 14/414602
DATED : January 21, 2020
INVENTOR(S) : John Lawrence Rowe Page 1 of 1

It is certified that error appears in the above-identified patent and that said Letters Patent is hereby corrected as shown below:

In the Claims

In Claim 1, at Column 16, Line 45, delete ", on a weight basis,".

Signed and Sealed this
Twenty-eighth Day of July, 2020

Andrei Iancu
*Director of the United States Patent and Trademark Office*